US009498356B2

(12) United States Patent
Lavelle et al.

(10) Patent No.: US 9,498,356 B2
(45) Date of Patent: Nov. 22, 2016

(54) FLEXIBLE STENT AND DELIVERY SYSTEM

(71) Applicant: Cook Medical Technologies LLC, Bloomington, IN (US)

(72) Inventors: Shay Joseph Lavelle, Annacotty (IE); Paul D. Devereux, Dublin (IE)

(73) Assignee: Cook Medical Technologies, LLC, Bloomington, IN (US)

( * ) Notice: Subject to any disclaimer, the term of this patent is extended or adjusted under 35 U.S.C. 154(b) by 0 days.

(21) Appl. No.: 14/106,157

(22) Filed: Dec. 13, 2013

(65) Prior Publication Data
US 2014/0172065 A1 Jun. 19, 2014

Related U.S. Application Data

(60) Provisional application No. 61/739,356, filed on Dec. 19, 2012.

(51) Int. Cl.
A61F 2/88 (2006.01)
A61M 27/00 (2006.01)
A61F 2/04 (2013.01)
A61F 2/95 (2013.01)

(52) U.S. Cl.
CPC .............. A61F 2/88 (2013.01); A61M 27/008 (2013.01); A61F 2002/041 (2013.01); A61F 2002/048 (2013.01); A61F 2002/9505 (2013.01)

(58) Field of Classification Search
CPC ...... A61F 2/88; A61F 2002/047; A61F 2/04; A61F 2002/041; A61F 2/042; A61M 27/008
See application file for complete search history.

(56) References Cited

U.S. PATENT DOCUMENTS

| 2,264,988 A | 12/1941 | Lee |
| 3,514,791 A | 6/1970 | Sparks |
| 4,003,369 A | 1/1977 | Heilman et al. |
| 4,080,706 A | 3/1978 | Heilman et al. |
| 4,295,464 A | 10/1981 | Shihata |
| 4,299,226 A | 11/1981 | Banka |
| 4,581,019 A | 4/1986 | Curelaru et al. |

(Continued)

FOREIGN PATENT DOCUMENTS

| CA | 2 264 988 A1 | 8/1999 |
| DE | 3314755 A1 | 4/1983 |

(Continued)

OTHER PUBLICATIONS

Extended European Search Report for Application No. 13197500.5, date of issuance Nov. 4, 2014.

(Continued)

Primary Examiner — Thomas J Sweet
Assistant Examiner — Daniel Bissing
(74) Attorney, Agent, or Firm — Brinks Gilson & Lione

(57) ABSTRACT

A stent is provided. The stent includes an elongate body comprising a tightly coiled wire disposed therealong, the coiled wire spanning between a first end portion and a second end portion, and defining a lumen therethrough. A safety wire is disposed through the lumen and fixed with respect to each of the first and second end portions. Proximal and distal end caps are fixed to the ends of the safety wire. At least one of the proximal and distal end caps comprises a window configured to receive the safety wire therethrough, and configured to allow access to the safety wire to weld the safety wire and the respective end cap.

16 Claims, 13 Drawing Sheets

(56) References Cited

U.S. PATENT DOCUMENTS

| | | | |
|---|---|---|---|
| 4,666,442 A | 5/1987 | Arru et al. |
| 4,693,242 A | 9/1987 | Biard |
| 4,713,049 A | 12/1987 | Carter |
| 4,738,666 A | 4/1988 | Fuqua |
| 4,787,884 A | 11/1988 | Goldberg |
| 4,813,925 A | 3/1989 | Anderson, Jr. et al. |
| 4,820,262 A | 4/1989 | Finney |
| 4,913,683 A | 4/1990 | Gregory |
| 4,930,496 A | 6/1990 | Bosley, Jr. |
| 4,931,037 A | 6/1990 | Wetterman |
| 4,957,479 A | 9/1990 | Roemer |
| 4,994,033 A | 2/1991 | Shockey et al. |
| 5,044,369 A | 9/1991 | Sahota |
| 5,160,341 A | 11/1992 | Brenneman et al. |
| 5,234,456 A | 8/1993 | Silvestrini |
| 5,254,104 A | 10/1993 | Furlow et al. |
| 5,323,768 A | 6/1994 | Saito et al. |
| 5,334,185 A | 8/1994 | Gisey et al. |
| 5,359,991 A | 11/1994 | Takahashi et al. |
| 5,405,334 A | 4/1995 | Roth et al. |
| 5,441,516 A | 8/1995 | Wang et al. |
| 5,554,189 A | 9/1996 | De La Torre |
| 5,558,643 A | 9/1996 | Samson et al. |
| 5,582,619 A | 12/1996 | Ken |
| 5,601,591 A | 2/1997 | Edwards et al. |
| 5,643,254 A | 7/1997 | Scheldrup et al. |
| 5,681,274 A | 10/1997 | Perkins et al. |
| 5,766,192 A | 6/1998 | Zacca |
| 5,865,723 A | 2/1999 | Love |
| 5,964,744 A | 10/1999 | Balbierz et al. |
| 6,033,413 A | 3/2000 | Mikus et al. |
| 6,096,034 A | 8/2000 | Kupiecki et al. |
| 6,120,522 A | 9/2000 | Vrba et al. |
| 6,162,231 A | 12/2000 | Mikus et al. |
| 6,254,592 B1 * | 7/2001 | Samson et al. ............ 606/1 |
| 6,264,611 B1 | 7/2001 | Ishikawa et al. |
| 6,280,457 B1 * | 8/2001 | Wallace ............ A61B 17/12022 606/191 |
| 6,332,892 B1 | 12/2001 | Desmond et al. |
| 6,371,979 B1 | 4/2002 | Beyar et al. |
| 6,383,146 B1 | 5/2002 | Klint |
| 6,395,021 B1 | 5/2002 | Hart et al. |
| 6,458,119 B1 | 10/2002 | Berenstein et al. |
| 6,517,569 B2 | 2/2003 | Mikus et al. |
| 6,589,262 B1 | 7/2003 | Honebrink et al. |
| 6,652,536 B2 * | 11/2003 | Mathews et al. ............ 606/113 |
| 6,654,536 B2 | 11/2003 | Battey et al. |
| 6,685,744 B2 | 2/2004 | Gellman et al. |
| 6,702,846 B2 | 3/2004 | Mikus et al. |
| 6,733,536 B1 | 5/2004 | Gellman |
| 6,736,839 B2 | 5/2004 | Cummings |
| 6,746,489 B2 | 6/2004 | Dua et al. |
| 6,770,101 B2 | 8/2004 | Desmond, III et al. |
| 6,887,215 B2 | 5/2005 | McWeeney |
| 7,044,981 B2 | 5/2006 | Liu et al. |
| 7,108,655 B2 | 9/2006 | Whalen et al. |
| 7,412,993 B2 | 8/2008 | Tzeng |
| 7,637,863 B2 | 12/2009 | Deal et al. |
| 7,731,693 B2 | 6/2010 | Melsheimer |
| 7,811,238 B2 | 10/2010 | Melsheimer et al. |
| 7,959,554 B2 | 6/2011 | McAlexander et al. |
| 8,022,331 B2 | 9/2011 | Reynolds et al. |
| 8,137,291 B2 | 3/2012 | Melsheimer |
| 8,211,118 B2 | 7/2012 | Catanese, III et al. |
| 2001/0018574 A1 | 8/2001 | Toledo et al. |
| 2002/0183852 A1 | 12/2002 | McWeeney |
| 2003/0018306 A1 | 1/2003 | Bucay-Couto et al. |
| 2004/0078088 A1 | 4/2004 | Gellman |
| 2004/0087886 A1 | 5/2004 | Gellman |
| 2004/0093075 A1 | 5/2004 | Kuehne |
| 2004/0127918 A1 | 7/2004 | Nikolchev et al. |
| 2004/0181186 A1 | 9/2004 | Gellman et al. |
| 2004/0193141 A1 * | 9/2004 | Leopold ............ A61F 2/88 604/527 |
| 2004/0267213 A1 | 12/2004 | Knapp |
| 2005/0033403 A1 | 2/2005 | Ward et al. |
| 2005/0075538 A1 | 4/2005 | Banik et al. |
| 2005/0222581 A1 | 10/2005 | Fischer, Jr. et al. |
| 2005/0234388 A1 | 10/2005 | Amos et al. |
| 2005/0240278 A1 | 10/2005 | Aliski et al. |
| 2006/0079926 A1 | 4/2006 | Desai et al. |
| 2006/0095050 A1 | 5/2006 | Hartley et al. |
| 2006/0149359 A1 | 7/2006 | Richter et al. |
| 2007/0021840 A1 | 1/2007 | Lopera |
| 2007/0050006 A1 | 3/2007 | Lavelle |
| 2007/0078446 A1 | 4/2007 | Lavelle |
| 2007/0078511 A1 | 4/2007 | Ehr et al. |
| 2007/0191767 A1 | 8/2007 | Hennessy et al. |
| 2007/0276466 A1 * | 11/2007 | Lavelle et al. ............ 623/1.22 |
| 2008/0086215 A1 | 4/2008 | St. Pierre |
| 2008/0133025 A1 | 6/2008 | Daignault et al. |
| 2008/0183299 A1 | 7/2008 | Monga et al. |
| 2008/0208083 A1 | 8/2008 | Lin et al. |
| 2010/0130815 A1 | 5/2010 | Gross et al. |
| 2010/0305715 A1 * | 12/2010 | Mathis ............ A61B 1/2676 623/23.65 |
| 2011/0276121 A1 * | 11/2011 | Levine ............ A61F 2/95 623/1.12 |
| 2013/0197623 A1 * | 8/2013 | McHugo ............ A61F 2/852 623/1.18 |

FOREIGN PATENT DOCUMENTS

| | | |
|---|---|---|
| DE | 20 2005 001 416 U1 | 1/2005 |
| EP | 0 054357 B1 | 11/1981 |
| EP | 0 213 748 A1 | 7/1986 |
| EP | 0 266 091 A2 | 10/1987 |
| EP | 0 266 091 A3 | 10/1987 |
| EP | 0 418 381 A1 | 9/1988 |
| EP | 0 365 269 A1 | 10/1989 |
| EP | 0 365 269 B1 | 10/1989 |
| EP | 0 516 189 A1 | 10/1989 |
| EP | 0 516 189 B1 | 10/1989 |
| EP | 0 672 394 A1 | 2/1995 |
| EP | 0 806189 A1 | 5/1997 |
| FR | 2 512 678 | 9/1982 |
| GB | 2 127 294 A | 9/1983 |
| JP | 2004248886 A | 2/2003 |
| WO | WO 90/14804 | 5/1990 |
| WO | WO 93/25265 | 6/1993 |
| WO | WO 97/24081 | 12/1996 |
| WO | WO 97/36536 | 4/1997 |
| WO | WO 00/66032 | 4/2000 |
| WO | WO 01/91668 A1 | 5/2001 |
| WO | WO 03/079930 A1 | 3/2003 |
| WO | WO 2005/096915 A1 | 3/2005 |
| WO | WO 2007/027830 A1 | 8/2006 |
| WO | WO 2009/023720 A1 | 8/2008 |

OTHER PUBLICATIONS

Wah, Tze M. and Irving, Henry C.; "A New Design for a Metallic Stent for the Management of Malignant Ureteral Obstruction"; European Renal & Genito-Urinary Disease 2006; pp. 93, 94, 96.

Flexor DL® Dual Lumen Ureteral Access Sheath, https://www.cookmedical.com/product/-/catalog/display?ds=uro_fusdl_webds, Sep. 30, 2013, 2 pgs.

Flexor® Ureteral Access Sheath, https://www.cookmedical.com/product/-/catalog/display?ds=uro_fus_webds, Sep. 30, 2013, 2 pgs.

Cook® 810 Set, https://www.cookmedical.com/product/-/catalog/display?ds=uro_cook810_webds; Sep. 30, 2013, 1 pg.

* cited by examiner

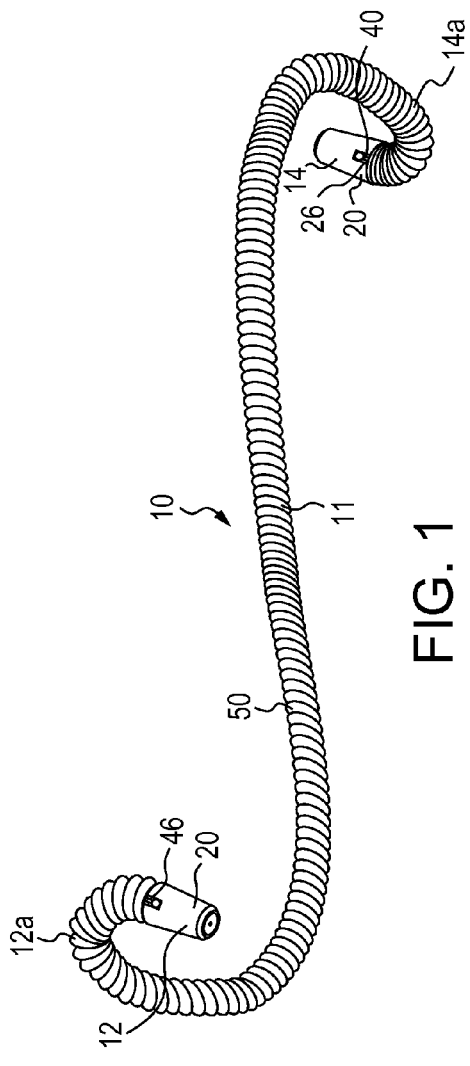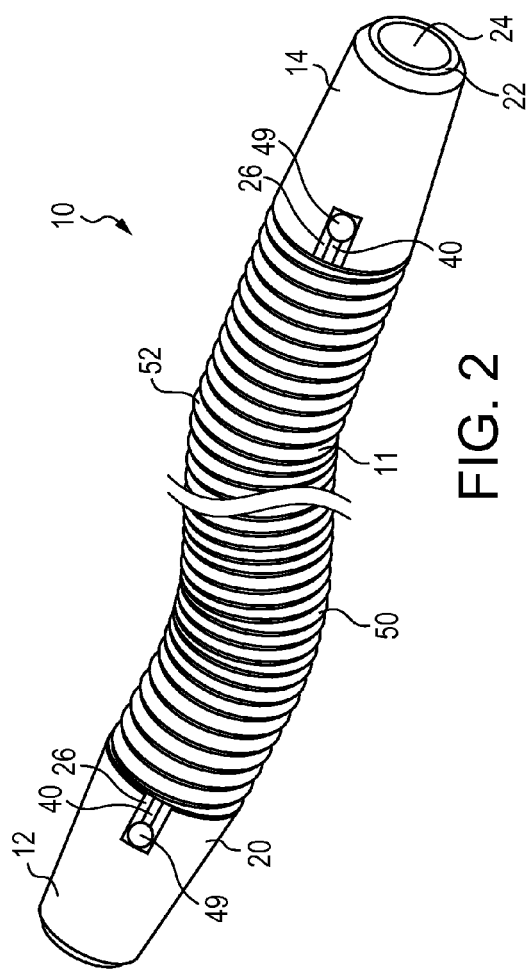

FLEXIBLE STENT AND DELIVERY SYSTEM

CROSS-REFERENCE TO RELATED APPLICATIONS

This application claims priority from U.S. Provisional Application No. 61/739,356, filed Dec. 19, 2012, the entirety of which is hereby fully incorporated by reference herein.

TECHNICAL FIELD

This subject disclosure is related to medical stents for opening and maintaining patency within a lumen within a patient, such as a ureter, a bile duct, or similar elongate and relatively narrow lumen within a patient's anatomy.

BRIEF SUMMARY

A first representative embodiment of the disclosure includes a stent. The stent includes an elongate body comprising a tightly coiled wire disposed therealong, the coiled wire spanning between a first end portion and a second end portion, and defining a lumen therethrough. A safety wire is disposed through the lumen and fixed with respect to each of the first and second end portions of the coiled wire. A proximal end cap is fixed to the proximal end of the safety wire and a distal end cap fixed to the distal end of the safety wire, each of the proximal and distal end caps are fixed with respect to the respective proximal and distal ends of the coiled wire. At least one of the proximal and distal end caps comprises a window configured to receive the safety wire therethrough, and configured to allow access to the safety wire to join the safety wire and the respective end cap.

Another representative embodiment of disclosure includes another stent. The stent includes an elongate body and first and second end portions. The elongate body includes a central portion comprising a plurality of neighboring rings disposed along the length thereof, with neighboring rings connected with a bar along voids established between neighboring rings. A single bar connects each neighboring ring and establishes a uniform distance between each neighboring ring along the length of the central portion. One or both of the ends of the stent are formed from a coiled wire, with an end that is attached to the central portion and an opposite end extending therefrom. The end may be formed into a pigtail or another arcuate orientation to provide fixation of the stent within the anatomy.

Another representative embodiment of a stent is provided. The stent includes an elongate central portion comprising a coiled wire disposed to define a plurality of coils disposed proximate to each other along a length of a stent between proximal and distal end portions with a lumen disposed therethrough, the plurality of coils each coiled to form a first outer diameter. A safety wire is disposed through the lumen of the stent and is fixed with respect to each of the proximal end portion of the coiled wire and the distal end portion of the coiled wire, wherein the safety is fixed to one or both of the proximal and distal end portions. The proximal end portion of the coiled wire further comprises one or more end coils, wherein an outer diameter of the one or more end coils is less than the first outer diameter.

Yet another representative embodiment of the disclosure is provided. The embodiment is a system for deploying a stent. The system includes an elongate stent defined from an elongate coiled wire defining proximal and distal end portions and a lumen therein and a sheath receiving the stent in a proximal portion of a sheath lumen extending therethrough. The sheath defines a side aperture that allows communication between the sheath lumen, and a ramp surface disposed within the lumen and proximate to the side aperture.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

BRIEF DESCRIPTION OF THE DRAWINGS

FIG. 1 is a side view of a stent.
FIG. 2 is a partial view of both proximal and distal ends of the stent of FIG. 1.

DETAILED DESCRIPTION OF THE DRAWINGS AND THE PRESENTLY PREFERRED EMBODIMENTS

Figure 3:
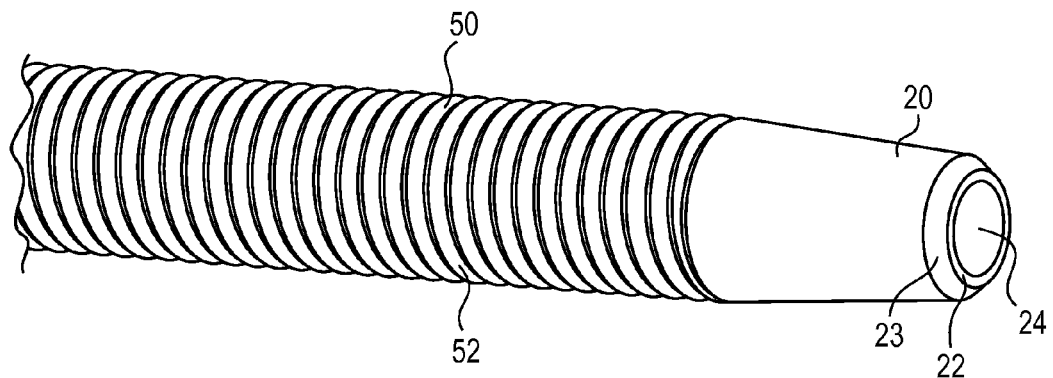
FIG. 3 is detail perspective view of an end portion of the stent of FIG. 1.
Figure 4:
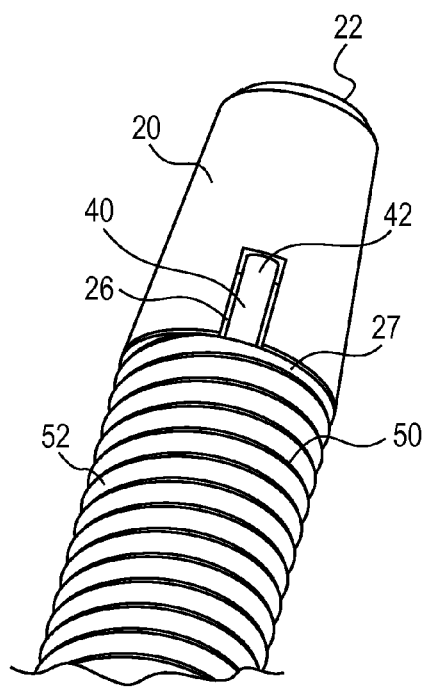
FIG. 4 is another detail perspective view of an end portion of the stent of FIG. 1.
Figure 5:
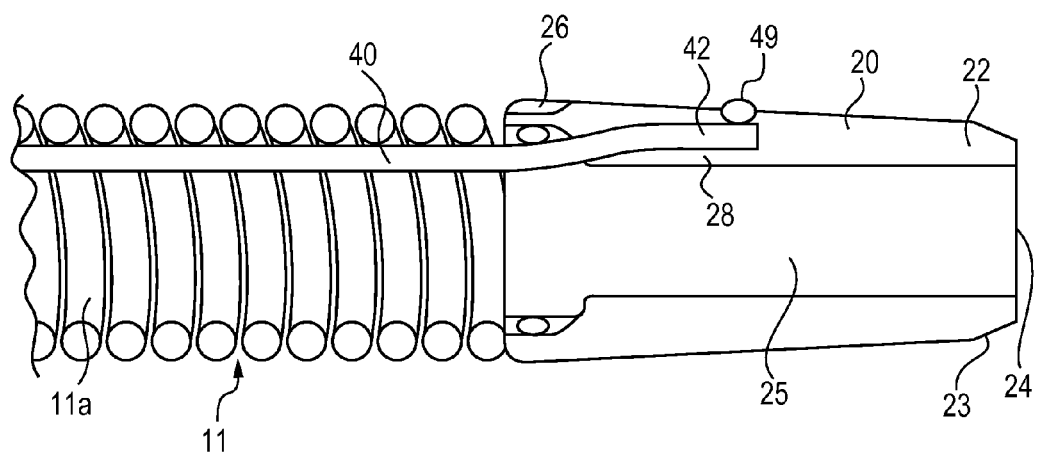
FIG. 5 is a sectional view of the end portion of FIG. 3.

Turning now to FIGS. 1-5, a first representative embodiment of a stent 10 is provided. The stent 10 (as well as the other stent embodiments disclosed and depicted below) is configured to be inserted into a narrow and elongate lumen of a patient, in order to establish and maintain patency through the lumen of clinical interest. In some embodiments, the stent 10 may be especially applicable for a ureter, urethra, a bile duct, or other application. In some embodiments, the stent 10 may be applicable for vascular applications.

The stent 10 includes a central portion 11 that extends between opposite first and second end portions 12, 14. The central portion 11 includes a lumen 11*a* (FIG. 5) disposed therethrough that allows for fluid communication therethrough, and through apertures 24 (aperture formed on the first end portion 12 is similar to aperture 14 depicted in FIG. 2) that are disposed through ends of the respective first and second end portions 12, 14. Fluid communication through with and through the lumen 11*a* is also possible through gaps provided between neighboring portions 52 of a tightly coiled wire 50 that defines the central portion 11, especially when the central portion 11 of the stent 10 is curved when placed within a patient's anatomy, such as through their ureter.

The central portion 11 of the stent 10 may be formed from a tightly coiled wire 50, with a plurality of coils 52 forming the coiled wire 50 disposed to define the lumen 11*a* extending therethrough as well as the structural outer flexible cylindrical surface of the stent 10. The coiled wire 50 may be formed such that neighboring coils 52 contact each other to provide for a lumen 11*a* that can maintain a flow of fluid therethrough, and to minimize and preferably eliminate the space between neighboring coils 52 to prevent tissue ingrowth, while the coiled wire 50 is sufficiently flexible (due to the size of the wire, the geometry of the coils, among other factors) to allow the central portion 11, and portions of the opposite first and second ends 12, 14 of the stent 10 that are defined by the coiled wire 50, to extend through a patient's urethra, and through a patient's ureter as the stent is inserted into the patient (by way of a delivery system) to be guided into place within the ureter. Moreover, the coiled wire 50 is configured to also be capable of forming pigtails 12*a*, 14*a* (FIG. 1) on one or both of the first and second ends 12, 14 of the stent 10. As is known in the art, one or two pigtails 12*a*, 14*a* may be provided on opposite ends of the stent 10 to provide a retention structure within the bladder for a proximal end of the stent 10 and an opposite retention structure within the kidney for the opposite distal end of the stent 10. In other embodiments where the stent 10 is used for clinical applications other than a patient's ureter, the stent 10 may be provided with or without pigtails as clinically and geometrically appropriate to retain the stent 10 in position as necessary.

One or both of the first and second ends 12, 14 of the stent 10 may include a cap 20, which may be disposed adjacent to or in contact with an end of the coiled wire 50. The cap 20 may include an aperture 24 disposed upon the outer end thereof with a lumen 25 disposed therethrough that is in communication with the lumen 11*a* through the central portion 11 of the stent 10. The presence of the lumen that extends through the length of the stent 10 and through both end caps 20 allows for the stent 10 to be delivered to the desired clinical location in an "over the wire" procedure, which is known to those of skill in the art. The cap 20 may be fixed directly to the coiled wire 50 (with adhesive, one or more weld joints, a press fit connection, or the like) or alternatively the cap 20 not be directly fixed to the end of the coiled wire 50. The cap 20 may include a window 26 (FIG. 4) that extends along a portion of the length of the cap 20, and may provide for communication with the lumen 20*a* of the cap 20. As discussed further below, the window 26 in the cap 20 may provide a pocket for an end of the safety wire 40 to be disposed therein, which allows for a convenient fixation or connection between the safety wire 40 and the cap 20.

The cap 20 may additionally include a proximal cuff that is next to the proximal end of the cap and receives an end of the coiled wire 50 therein. The cuff is provided to support the end of the coiled wire 50 within the cap 20, to prevent the coiled wire 50 from unwinding and to prevent the end of the coiled wire 50 from extending radially outside of the diameter of the stent 10.

In some embodiments, the cap 20 may include a tapered profile as the cap 20 approaches its tip 22, such as a conical profile that is formed like a geometric truncated cone or with another type of tapered profile. The design of a conical profile within the cap 20 may assist with deployment and positioning of the stent 10, such as the placement of a stent through a tortious path, or when the stent 10 is urged through a track that initially has a path with a smaller diameter than the diameter of the stent 10. The gradual expansion of the anatomical lumen through when the stent 10 is placed is urged by the conical shape of the stent 10. In some embodiments, the top 22 of the cap 20 may have a chamfered edge 23 or with another similar geometry to further provide a gradual transition for expanding the anatomical lumen through which the stent 10 is deployed.

In some embodiments, the cap 20 includes a window 26 that extends for a portion of a length of the cap 20, and provides an aperture for communication with the lumen 25 within the cap 20 from outside of the cap 20. The window 26 is configured to receive an end 42 of a safety wire 40 that extends through the lumen 11*a* of the central portion 11. As discussed in more detail below, the safety wire 40 is provided to prevent the coiled wire 50 from significantly stretching due to a fixation between opposite ends 42 of the safety wire 40 with opposite end portions of the coiled wire 50, either direct fixation, or indirect fixation between the two. The safety wire 40 prevents the coiled wire 50 from stretching, which may be clinically important in various situations, such as in situations where the proximal end of the stent 10 is retracted for removal after the stent 10 has been indwelling within the patient for a significant length of time.

The window 26 may be disposed from a proximal edge 27 of the cap 20 and blindly extend along the cap 20. The window 26 may be simply an elongate aperture (such as a rectangular aperture) that extends through the cap 20, while in other embodiments, the window 26 may further include a ledge 28 disposed at a distal end portion of the window 26 to support the end 42 of the safety wire 40. The window 26 (and ledge 28 when provided) is configured to receive an end 42 of the safety wire 40 therein and allow convenient fixation between the safety wire 40 and the cap 20. For example, in some embodiments, the tip 42 of the safety wire 40 may be welded, crimped, or otherwise affixed directly to the cap 20. This direct connection between the safety wire 40 and the cap 20 additionally causes the safety wire 40 to be fixably mounted with respect to the coiled wire 50 in view of the fixation between the respective end of the coiled wire 50 and the cap 20.

Figure 6:
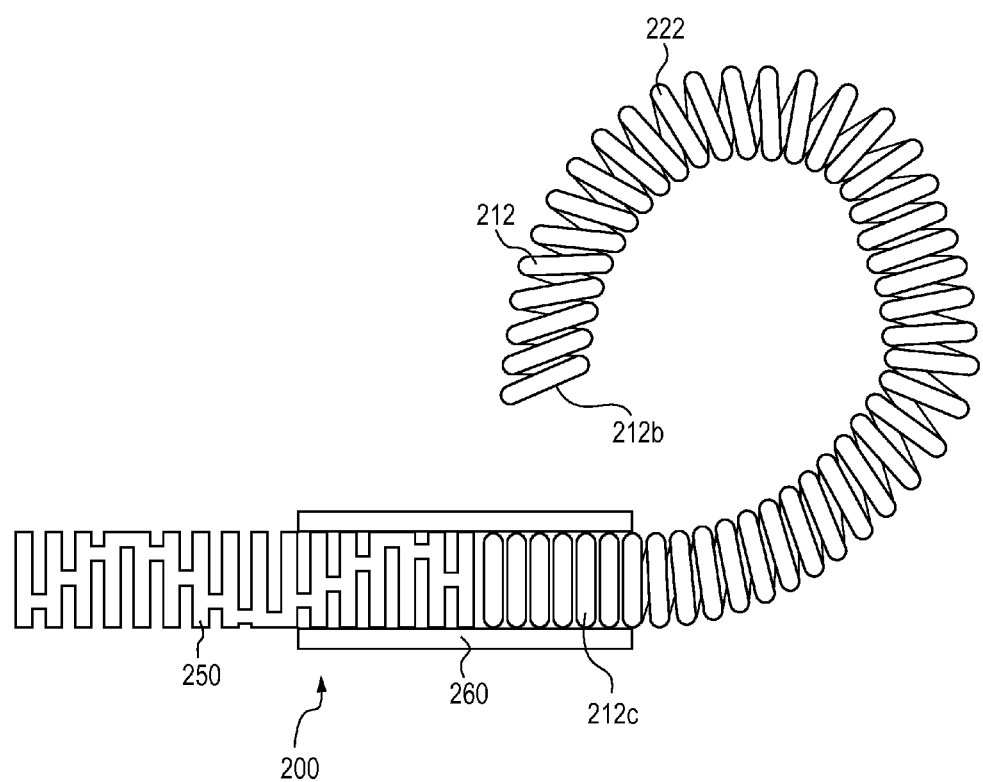
FIG. 6 is a side view of another stent.
Figure 7:
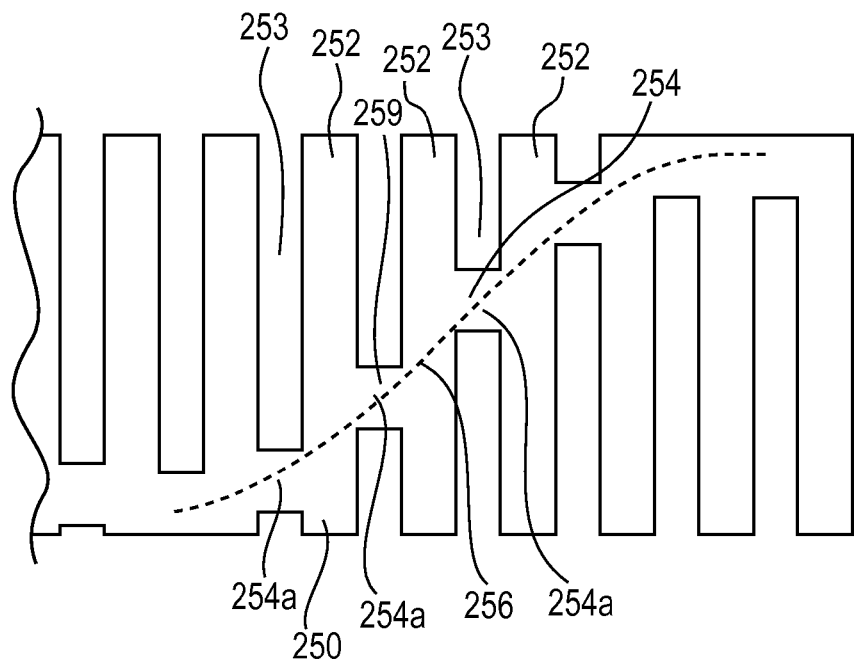
FIG. 7 is a side view of the central portion of the stent of FIG. 6.
Figure 8:
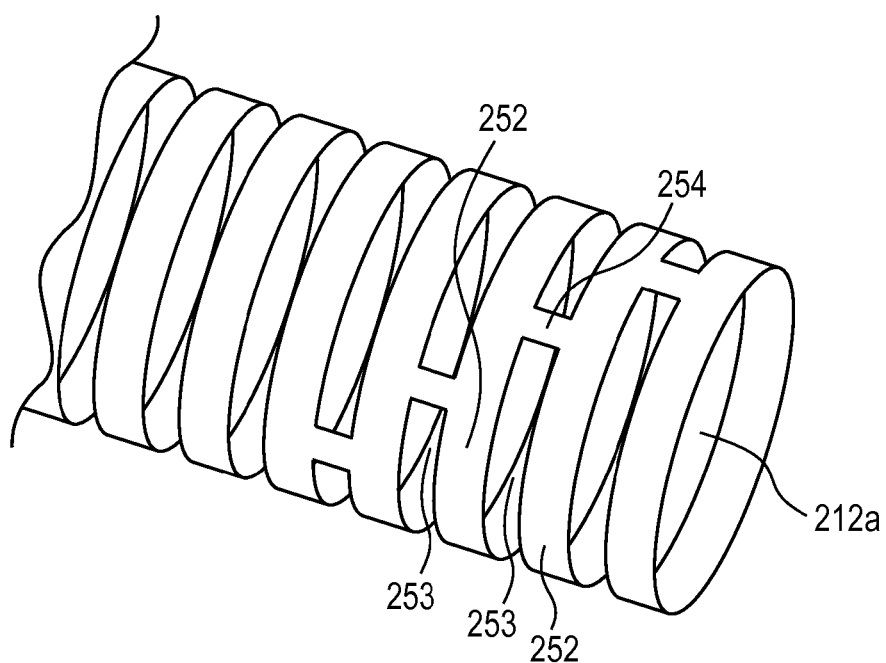
FIG. 8 is a perspective view of the central portion of the stent of FIG. 6.

Turning now to FIGS. 6-8, another representative stent 200 is provided. The stent 200 may include a central portion 250 and one or two end portions 212 that extend from the central portion 250. As discussed further below, the central portion 250 may be formed from a metallic cannula, such as one formed from a superelastic material, such as nitinol, or formed from other materials, such as stainless steel, or a cobalt chromium alloy. In some embodiments, the central portion might be formed from a single cannula and laser cut, chemically etched, or formed with another process known in the art, such that portions of the material are removed to develop a portions with material remaining, and portions with material removed.

As best shown in FIGS. 7 and 8, the central portion 250 may be processed or formed to include a plurality of spaced apart rings 252 that are disposed in parallel but spaced apart from each other between voids 253. In some embodiments, the neighboring rings 252 may be connected with preferably one, but potentially more than one, bars 254 to maintain the horizontal alignment between neighboring rings 252. In some embodiments, consecutive bars 254 may be aligned at different positions along the outer circumference of the central portion 250. For example, consecutive bars 254 may be aligned at rotational intervals along the length of the central portion 250, such that a line 256 (broken line, FIG. 7) through the centers 254a of each bar 254 travels helically along the central portion 250. As can be understood with reference to the subject specification, the helical arrangement of bars 254 along the length of the central portion 250 provides for increased flexibility of the central portion 250 than other embodiments, such as embodiments where the neighboring bars 254 are disposed along the same circumferential position along the length of the central portion 250, or embodiments where two or more bars connect neighboring rings 252. In some embodiments, the bars 254 are significantly more narrow than the width of the rings 252 that are separated by the bars, such as one half, one tenth, or one twentieth of the width of the rings 252. In other embodiments, the bars 252 may be about the same as the width of the rings 252. One of ordinary skill will understand upon review of this specification that the stent may be designed to minimize the space between neighboring rings (for such purposes as minimizing tissue ingrowth or maintain a lumen through the stent, among others).

The end portions 212 are fixed to the central portion 250. The end portions 212 may be made from a single coiled wire, such as a stainless steel, cobalt chromium (CoCr) wire, with a tight coil to provide substantially the same outer diameter as the central portion 250. In some embodiments, the end portions 212 and the central portion 250 may be manufactured to be about 3 Fr (1 mm), while in other embodiments the central and end portions 250, 212 may be about 6 Fr (2 mm) or other dimensions therebetween, or larger depending upon the desired clinical use. It is known that a 6 Fr diameter is clinically appropriate for many ureteral stent applications, while embodiments with smaller embodiments, such as 3 Fr, may be clinically appropriate (i.e. to provide the necessary lumen for sufficient urine flow therethrough) to provide patency through severely blocked ureteral passageways, which may not be clinically appropriate for a 6 Fr stent.

In some embodiments, the end portions 212 are formed from a coiled wire, which is tightly wound to the outer diameter of the central portion 250 of the stent. The end portions 212 may be trained to retain a pigtail shape (FIG. 6) to provide one or both of the proximal and distal ends of the stent with retention structures, such as to aid in retaining the distal end of the stent within the kidney and the proximal end the stent within the bladder. In some embodiments, the end portions 212 are formed without a safety wire therethrough (and connected to the outer tip 212b), because stretching is not a concern in the pigtail or otherwise arcuate end portions 212. In other embodiments, one or both end portions 212 may be formed with an internal safety wire which extends through the lumen of 212a of the end portion, with opposite ends of the safety wire fixed proximal to the outer tip 212b of the end portion 212 and the inner tip 212c of the end portion 212. The safety wire may be formed from the same material or a different material than the coiled wire forming the end portion 212, and may be substantially thin to not block a significant percentage of the lumen 212a therewithin. In embodiments where a safety wire is provided, the safety wire may be trained to maintain the pigtail or other retention configuration along with remainder of the end portion 212, such as bending the end portion 212 into the desired orientation, and/or using conventional nitinol "shape training" techniques as known in the art. In still other embodiments, the end portions 212 may be formed from a laser cut cannula, similar to the construction of the central portion 250.

In some embodiments, the one or two end portions 212 are fixed directly to the central portion 250, such as by various joining methods, such as soldering or welding (laser welding or other conventional techniques) the inner tip 212c to an end of the central portion 250, or otherwise fixing them together. In some embodiments the two components may be fixed together with a shrink fit sleeve 260, as shown in FIG. 6, which may be in addition or instead of the welding between the two.

Figure 9:
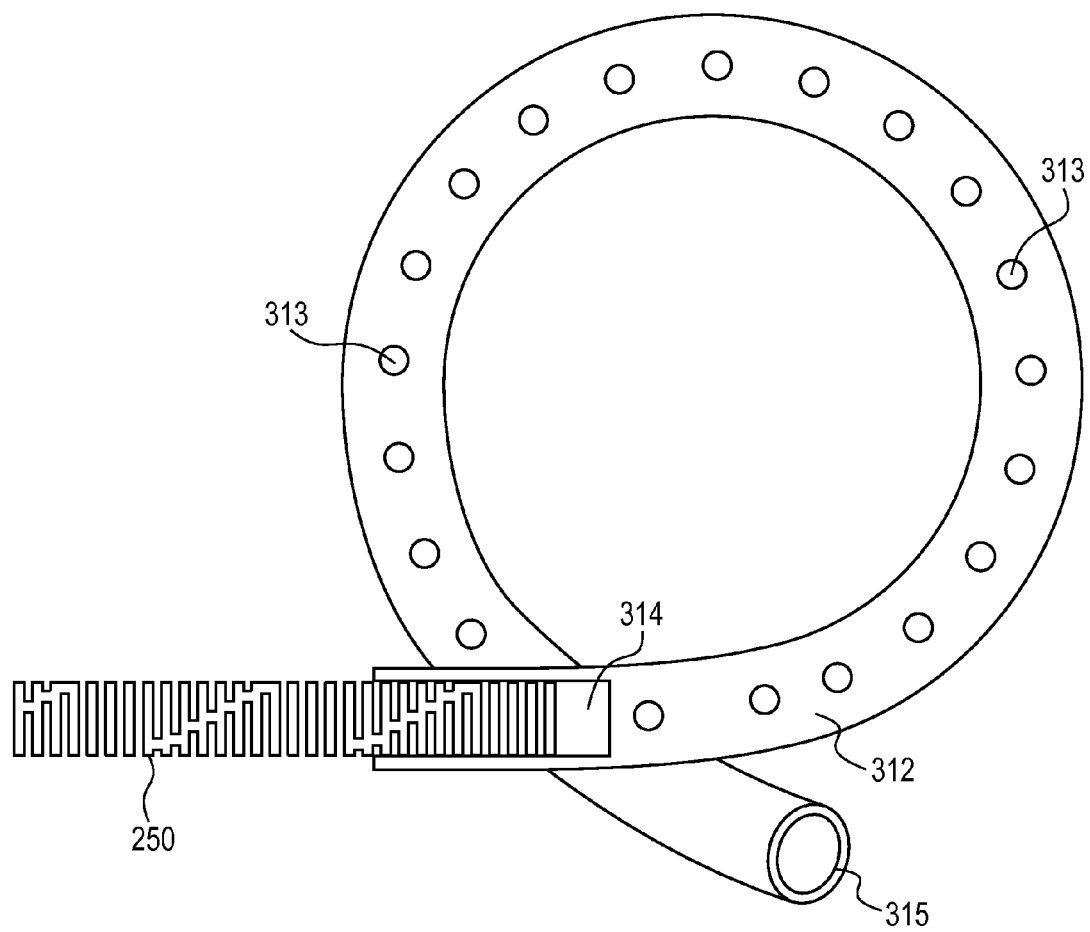
FIG. 9 is a side view of an end portion of another stent.

In other embodiments shown in FIG. 9, alternate end portions 312 may be provided upon one or both ends of the central portion 250. The end portions 312 may comprise plastic pigtail sections, such as sections found in conventional plastic ureteral stents. Each end portion 312 may be thermally bonded to the respective end of the central portion 250. The end portions 312 may include a closed end, or as shown in FIG. 9, an open end 315 allowing fluid communication within the lumen 314 through the end. The end portions 312 may additionally include a plurality of apertures 313 that allow fluid communication into the lumen 314.

Figure 10:
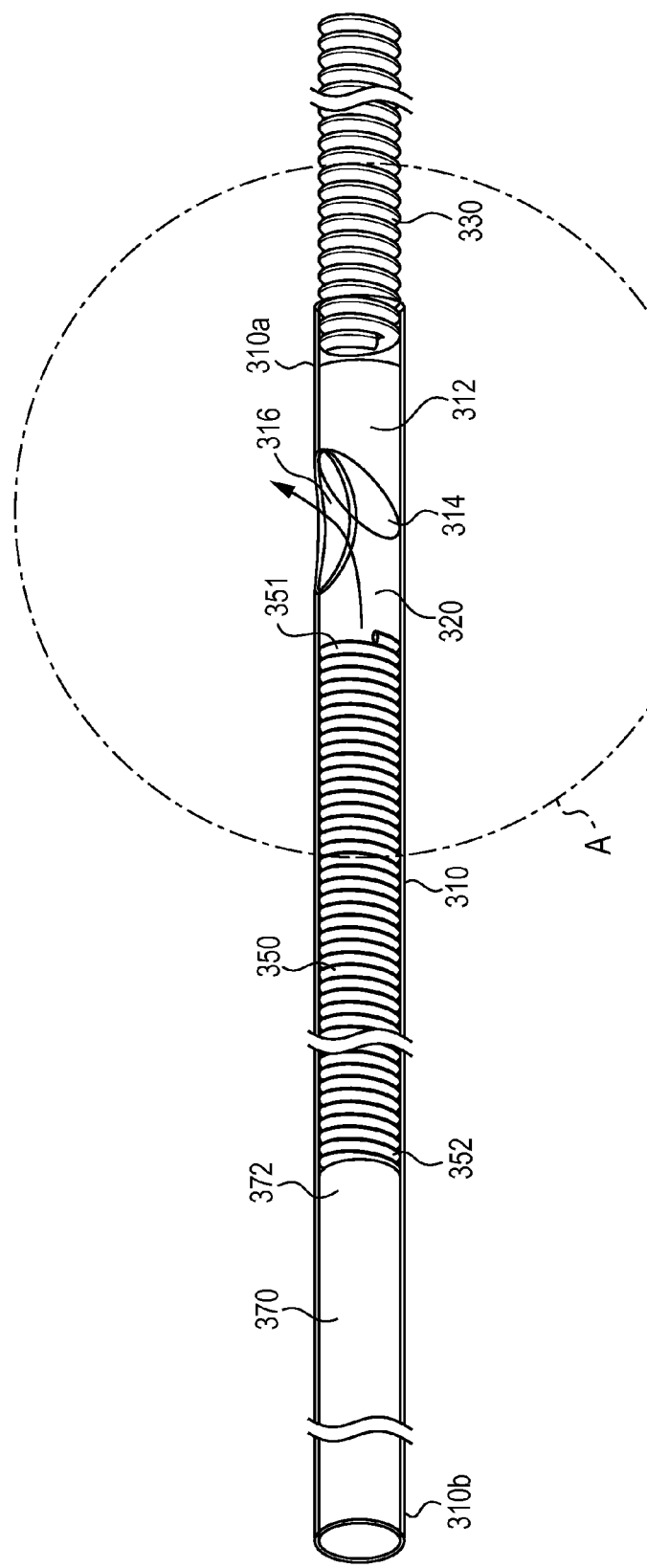
FIG. 10 is a side view of a stent deployment system.
Figure 11:
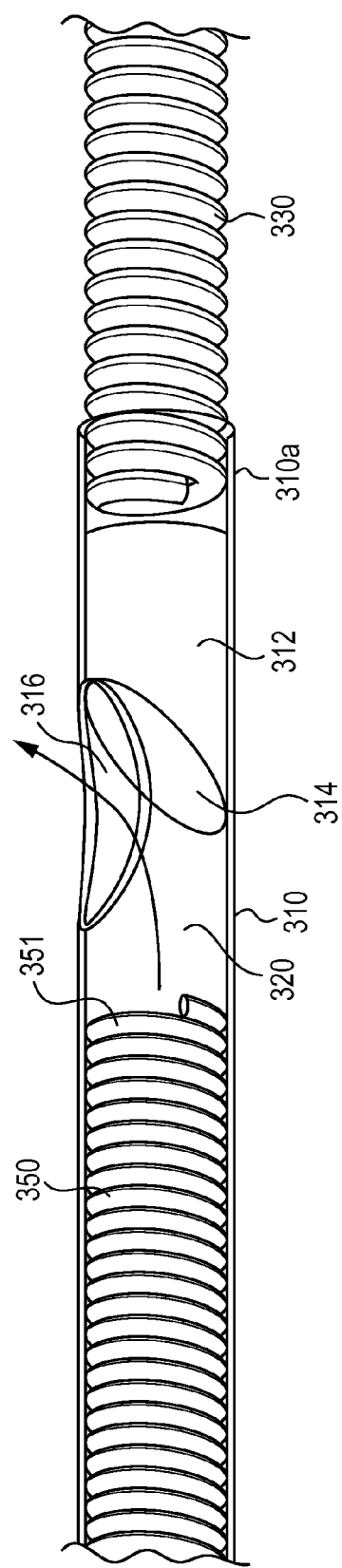
FIG. 11 is a detail view of detail A of the stent deployment system of FIG. 10.
Figure 12:
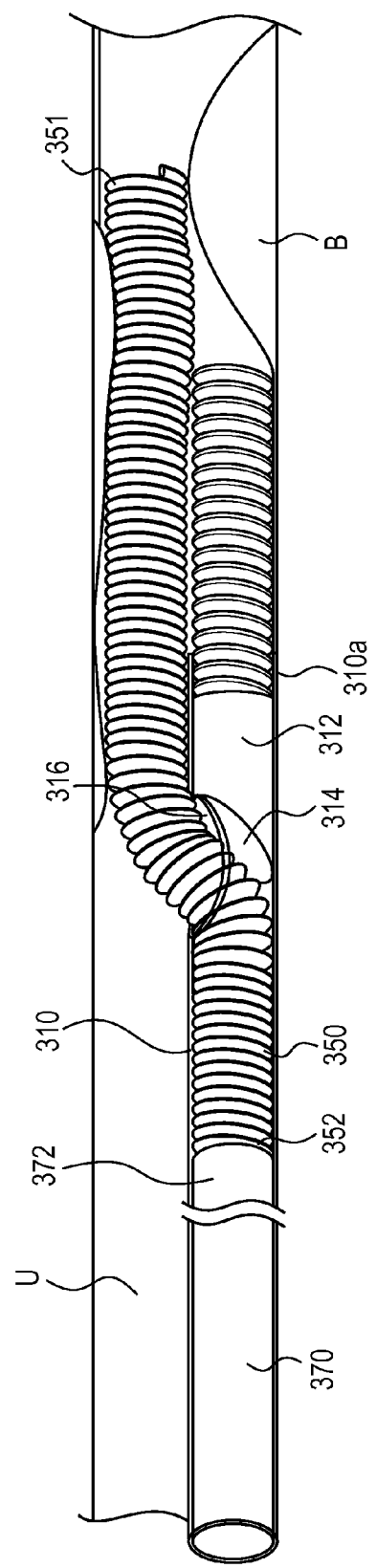
FIG. 12 is a detail view of detail A of the stent deployment system of FIG. 10.

Turning now to FIGS. 10-12, a sheath 310 for deploying a stent 350 is provided. The stent 350 may be like one or more of the stents described above, or may be another type of elongate flexible stent known in the art. In some embodiments, the stent 350 may be formed from a tightly coiled wire, such as a nitinol, stainless steel, cobalt chrome alloy or other types of wire, and extend from a distal end portion 351 to a proximal end portion 352 with a lumen disposed therethrough. In some embodiments, the stent 350 may be formed with a coiled wire that is sufficient flexible to traverse the tight curves of a patient's urethra and ureter to be implanted into a desired position within the anatomy, such as through a patient's ureter. In some embodiments, the stent 350 is configured such that neighboring coils contact each other at one or more locations along each neighboring coil, but provide small spaces between neighboring coils, especially when the stent 350 is along a curved anatomy, to allow fluid from outside of the stent 350 to pass into the lumen of the stent 350 and flow therethrough. In some embodiments, the stent 350 may have an outer diameter of about 3 Fr (1 mm) and be configured to be retained within a ureter, and in some embodiments with one or both of the distal and proximal end portions 351, 352 biased toward an arcuate, or "pigtail" orientation to be retained within the kidney (distal end portion 351) and the bladder (proximal end portion 352) to retain the stent 350 within the ureter. In embodiments where the stent 350 is about 3 Fr (1 mm) the stent 350 is configured to achieve patency through the ureter, especially in situations where ureter is blocked such that patency is difficult therethrough with conventional ureteral stents, such as 6 Fr (2 mm) stents.

The sheath 310 is a flexible elongate member that extends between distal and proximal ends 310a, 310b with a lumen therethrough. The lumen is configured to receive the stent 350 slidably therein, as best shown in FIGS. 10 and 11. The sheath 310 additionally slidably receives the distal portion of a pusher 370 which is disposed proximal to the proximal end portion 352 of the stent 350, such that distal movement of the pusher 370 (as urged by the medical professional) causes similar distal motion of the stent 350.

The sheath 310 further comprises a block 312 disposed proximate to the distal end portion 310 of the sheath 310. The distal block 312 forms the distal end of the lumen and may include a ramp surface 314 disposed within the lumen and facing proximally within the lumen. The ramp surface 314 is configured to receive the stent 350 as the stent 350 is urged distally within the sheath 310, and urges the stent 350 from movement through the lumen through an aperture 316 defined upon a sidewall of the sheath 310. Specifically, the aperture 316 is defined upon the sheath 310 such that the stent 350 extends through the aperture 316, and therefore out of the sheath 310, as the stent 350 slides along the ramp surface 314.

The sheath 310 may include a flexible member 330, such as a filiform tip that is connected to the distal end portion 310a thereof, which is provided to direct the sheath 310 toward the selected clinical area for stent deployment, such as through the ureter U. In use, the sheath 310 may be advanced through the urethra, the bladder, and into the ureter using known positioning techniques. As the sheath 310 is directed through the ureter U, the filiform 330 aides in directing the sheath 310 toward the kidney, and or two a blockage or stricture B within the ureter U. As the sheath 310 approaches the desired position (as judged by the filiform position), the stent 350 is urged from the sheath 310 by pushing the pusher 370 distally. As the pusher 370 is pushed distally, the distal end of the pusher 370 engages the proximal end 352 of the stent 350, which pushes the stent 350 distally within the lumen of the sheath 310. With sufficient distal motion, the stent 350 engages the ramp surface 314 within the sheath 310 which urges the stent 350 out of the sheath 310 through the aperture 316 defined upon the side wall of the sheath 310. With continued distal motion, the stent 350 translates along the outer surface of the sheath 310 and filiform until the stent 350 is properly positioned within the ureter U, such as through the stricture B, or into the kidney (where the distal end portion 350 of the stent 350 may be biased toward an arcuate or pigtail configuration to retain the stent 350 properly positioned within the ureter U) to allow for patency through the blockage/stricture B through the lumen of the stent 350. After the stent 350 is properly positioned with respect to the ureter U and the kidney (if desired), the sheath 310 is retracted proximally with respect to the stent 350 and removed from the ureter U and ultimately the patient, with the stent 350 remaining in position. In some embodiments, the proximal end portion 352 of the stent 350 may extend into the bladder and may form an arcuate portion or a pigtail to further retain the stent 350 properly positioned within the ureter U.

Figure 13:
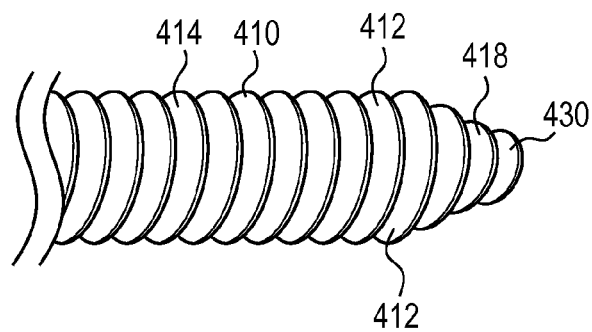
FIG. 13 is a side view of a proximal end portion of a stent.
Figure 14:
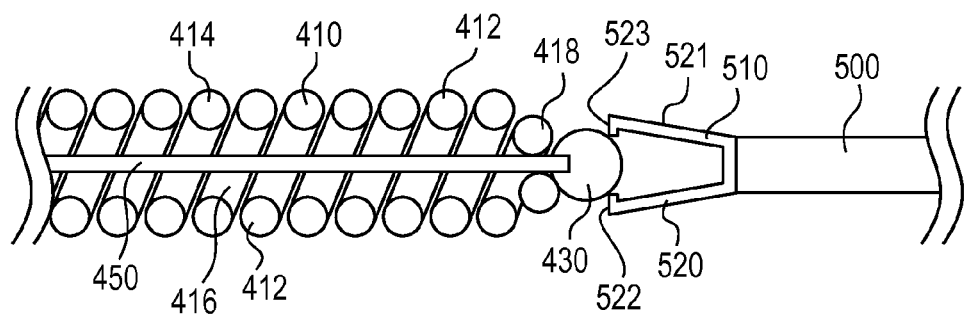
FIG. 14 is a sectional view of the stent of FIG. 13 with a grasper approaching the proximal end portion of the stent.
Figure 15:
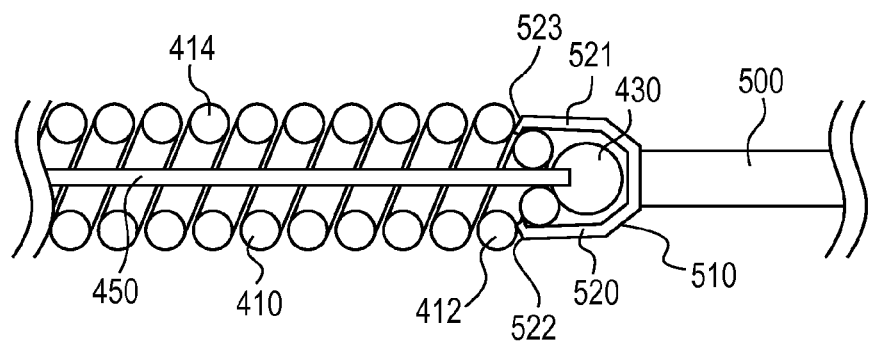
FIG. 15 is the view of FIG. 14 with the grasper engaging the proximal end portion of the stent.

Turning now to FIGS. 13-15, another embodiment of a stent 410 is provided. The stent 410 may extend between a proximal end portion 412 and a distal end portion (not shown, but similar to the proximal end portion 412). The stent 410 may be formed from a coiled wire to define a plurality of neighboring coils 414 that are tightly wound to provide patency to an anatomical lumen through which the stent 410 extends (such as a ureter, bile duct, or other similar lumen) as well as provide a flow path for fluid, such as urine therethrough, such as from the kidney to the bladder. The stent 410 may be formed with a safety wire 450 that extends through the lumen 416 of the stent 410 and may be fixed to (or with respect to) the distal and proximal end portions 412 of the stent 410. The safety wire 450 is normally not stretchable, and therefore prevents the coiled wire forming the stent from uncoiling during deployment, indwelling use, or particularly upon removal, when the proximal end portion 412 of the stent 410 is pulled proximally. In some embodiments, one or both of the distal and proximal end portions 412 of the stent 410 includes a weld bead 430, which fixes an end of the safety wire 450 with respect to the respective end portion of the stent 410.

In some embodiments, the weld bead 430 may be approximately the same diameter as the body of the stent 410, such as 3 Fr (1 mm), 6 Fr (2 mm) or other diameters that are configured for various desired clinical uses. In some embodiments, the final coil (such as the proximal-most coil 418, or the distal-most coil, like the proximal-most coil 418 depicted in the figures) is formed with an outer diameter less than the reminder of the coils 414 that define the body of the stent 410. For example, for stents 410 with a body portion with coils 414 that are each about 6 Fr, the proximal-most coil 418 and/or the distal-most coil may be formed at about 3 Fr, and preferably with a diameter smaller than the diameter of the weld bead 430 that fixes the end of the safety wire 450 to the end of the body of the stent 410.

As shown in FIG. 15, a grasper 510 with a pair (or set) of arms 520, 521 may be provided that is configured to engage the final coil 418 and weld bead 430 to allow for withdrawing a deployed stent 410 proximally. Each of the pair (set) of arms 520, 521 may include a respective tooth 522, 523 that is configured to engage the final coil 418, with the arms 520, 521 sized and configured to engage the outer surface of the weld bead 430. The grasper 510 may be connected to a control portion 500, such as a sheath or a control wire, which is manipulable by a user remotely from the proximal end portion 412 of the stent 410. In some embodiments, the pair (set) of arms 520, 521 of the grasper 510 are configured to be sufficiently resilient to bend around the weld bead 430 and engage the final coil 418 as the grasper 510 is urged toward and over the weld bead 430. The teeth 522, 523 are configured to engage one or both of the final coil 418 and the weld bead 430 to pull the stent 410 proximally with the grasper 510 as the grasper 510 is pulled proximally (as urged by the control portion 500).

As can be appreciated, the size of the final coil 418 and the weld bead 430 are configured, in combination with the arms 520, 521, to engage the proximal end 412 of the stent 410 with a total outer diameter that is substantially the same, or slightly smaller than the outer diameter of the body of the stent 410. This design will be appreciated to be especially configured to allow for grasping of a proximal end portion 412 of a stent 410 deployed tightly within a lumen, such as a ureter, especially in situations where the proximal end portion 412 of the stent 410 is disposed within the lumen. In some embodiments, the stent 410 is configured to be surrounded by a sheath (not shown) that is disposed over the stent through the entire length of the ureter and into the kidney (or potentially over a portion of the ureter, as clinically appropriate) with the stent 410 remaining within the ureter. The proximal end portion 412 is sized such that the grasper 500 engages the proximal end 412 of the stent 410, as discussed above, with the stent 410 disposed within the sheath. After engagement, the grasper may be withdrawn proximally, which simultaneously moves the stent 410 proximally, while the sheath is maintained within the ureter, and in some embodiments, with a portion of the sheath extending through the bladder, urethra, and out of the patient. After the stent 410 is fully removed from the patient through the sheath, a new stent 410 (or other stent design, configured for maintaining ureteral patency and/or drainage described elsewhere herein, or otherwise known in the art) may be threaded through the sheath and into position within the ureter (and kidney as appropriate) for convenient stent exchange. One of ordinary skill in the art, upon review of this disclosure, will appreciate that the design of smaller end coil 418 (or a plurality of smaller end coils 418), preferably in combination with a weld bead that 430 that is also smaller than the outer diameter of the body of the stent 410 allows for a grasper no larger than the diameter of the stent 410 to engage an pull proximally a deployed stent 410 for stent exchange through the sheath.

Turning now to FIGS. 16-19 a stent exchange system 600 is depicted. The stent exchange system 600 may include first and second sheaths 610, 620 which are configured for coaxial deployment, or may include only a first sheath 610. The first sheath 610 is an elongate, flexible sheath that extends from a distal end portion 611 to a proximal end portion (not shown), with a central portion 613 therebetween. The first sheath 610 may be sized to extend from within a patient's bladder, through the length of a typical patient's ureter, and into a patient's kidney. In other embodiments where the stent exchange system 600 is configured for use in other portions of the anatomy (such as, for example, the GI tract, the biliary tree, or potential for cardiovascular applications) the sizes and profiles of the first and second sheaths 610, 620 may be varied, in such a manner that will be easily appreciated by one of ordinary skill in the art would be appropriate after a thorough review and understanding of the subject specification and figures.

The first sheath 610 may include a substantially C-shaped profile along its length, and specifically along a central portion 613 thereof, such that material forming the side wall of the first sheath 610 extends along a significant portion (and greater than 180 degrees) of the arc length of a circle, and defines a cavity 618 therewithin, but defines a side opening 619 that extends along the length of the first sheath 610 and allows access into the cavity 618 through the side opening 619.

Figure 16:
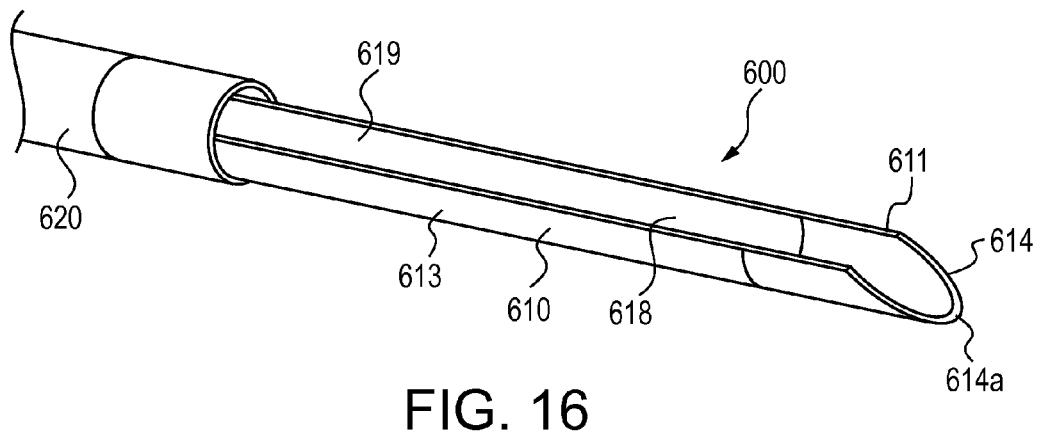
FIG. 16 is a perspective view of coaxial first and second sheaths for use in an indwelling stent exchange system.

In some embodiments, as shown in FIG. 16, the side opening 619 along the central portion 613 may be formed with an arc length (defining the arc length where the side wall of the first sheath 610 does not exist) of between about 45 degrees to about 150 degrees, and inclusive of all potential arc lengths therein. In other embodiments, such as the first sheath 610 depicted in FIG. 17, the side opening 619 along the central portion 613 may be very thin, such as between about 10 degrees to about 30 degrees arc length (inclusive of all potential arc lengths therein). In some embodiments, the arc length of the opening 619 is consistent along the central portion 613 of the first sheath 610, while in other embodiments, the arc length of the central portion 613 may vary along the length of the first sheath 610.

The first sheath 610 may include a scooped portion 614, or a bevel at the distal end thereof, which provides for a gradual increase in the arc length of the wall forming the first sheath 610 from the distal tip 614a (which has a relatively small arc length, such as about 30 to about 50 degrees) to the arc length of the side opening 619 about the central portion 613. In some embodiments, the increase in arc length of the side wall (and therefore a related decrease in arc length of the side opening 619) along the scooped portion 614 may be linear (as shown in FIG. 16) such that the opposed material edges of the side wall defining the scooped portion 614 lie along a plane that is at an acute angle with respect to the longitudinal axis of the first sheath 610. Alternatively, in other embodiments, the increase in arc length of the side wall of the first sheath 610 along the scooped portion 614 is at a non-constant rate (either an increasing rate as the arc length of the side wall along the scooped portion 614 increases, or a decreasing rate as the arc length of the side wall increases) to give the edges of the scooped portion 614 a non-planar profile.

The proximal end of the first sheath 610 may be formed with a scooped portion 614 that is like that depicted in FIG. 16 (or with the variations to the scooped portion 614 described above), or may be formed with a material edge (at the proximal end) that is perpendicular to the longitudinal axis of the first sheath 610. As discussed below, a scooped portion on the proximal end portion of the first sheath 610 may be desired for ease of threading the second sheath 620 over the proximal end portion of the first sheath 610 and ultimately along the entire length of the first sheath 610 and into the kidney (or in embodiments were only the first sheath 610 is used, for threading a replacement stent 700 through the scooped portion on the proximal end portion and into the cavity 618 for placement as clinically necessary.

The first sheath 610 may be formed from a relatively flexible material that allows for expansion of the side opening 619 as needed for interacting with a previously placed stent 700, while maintaining sufficient column or tube strength to maintain the ureter (or other clinical lumen for desired interaction by a stent) patent after the indwelling stent 700 is removed (discussed below). Suitable materials for the first sheath 610 may be FEP, PTFE, or other materials that are known to be significantly low in friction in a clinical setting. Further, sheaths with hydrophilic coatings may be used. In some embodiments, a distal end portion 614 of the first sheath may be echogenic or metal, and/or potentially with one or more coatings known in the art that allow for remote observation of the distal tip 614 of the first sheath 610 when deployed within the patient, such as via ultrasound, fluoroscopy, or other remote clinical observation tools. Similarly, a distal end portion of the second sheath 620, discussed below, may also be formed from, coated with, or processed such that it may be visible through ultrasound, fluoroscopy, or other clinical remote observation tools when deployed within the patient.

The second sheath 620 is an elongate sheath that extends between a distal end portion 620 and a proximal end portion (not shown) with a lumen therethrough. The second sheath 620 may be formed with an inner diameter just larger than a diameter of the first sheath 610 (measured across the first sheath 610 between two portions of the side wall that form the first sheath 610 (and not measured with respect to the side opening 619 of the first sheath 610). The second sheath 620 is configured to be slid over the first sheath 610, normally after the previously indwelling stent has been removed, such that the first sheath 610 (and in some embodiments an indwelling stent 700) is disposed within the lumen of the second sheath 620. The second sheath 620 may be sized such that a proximal end portion extends outside the patient (e.g. through the urethral meatus) when the distal end portion 621 extends into the kidney K. In some embodiments, the second sheath 620 may be formed from a clear material, such that the first sheath 610 or the stent 700 disposed therethrough may be observed through the side wall of the second sheath 620.

Figure 17:
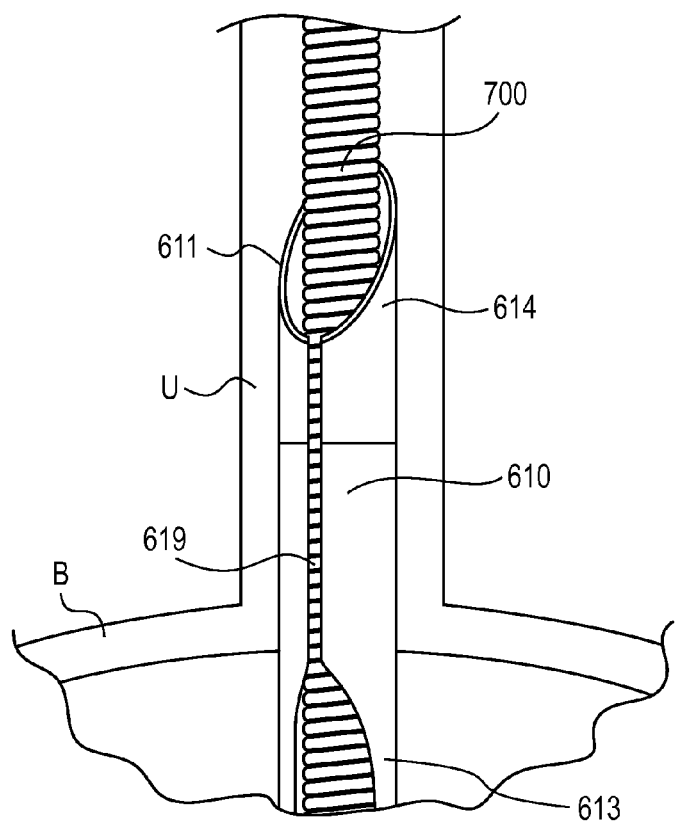
FIG. 17 is the system of FIG. 16, with the first sheath disposed partially over an indwelling stent and into the ureter.

As shown in FIGS. 17-21, the first and second sheaths 610, 620 may be used in tandem (or in some embodiments, only the first sheath 610 may be used) to allow for replacement of an indwelling ureteral stent 700 (or alternatively another type of indwelling stent within a different portion of a patient's anatomy, such as an indwelling stent that is formed without apertures on opposite sides of a stent and a lumen therethrough, such as one of the stents described in this specification and depicted in these drawings, or stents described in U.S. Pat. No. 7,550,012, commonly assigned to the assignee of the subject application, or another indwelling stent known in the art). When an indwelling stent (depicted as 700 in FIG. 17) is desired to be replaced by a new stent (such as when the indwelling stent 700 is determined to be at the end of its useful or indicated life, or for other reasons) the first sheath 610 may approach a portion of the indwelling stent 700 that extends into the bladder B (such as a portion of the stent 700 extending just through out of the ureter U and into the bladder B. The first sheath 610 is guided toward the stent 700, such that the scooped portion 614 engages the stent 700 causing the stent 700 to be aligned with respect to the cavity 618 within the first sheath 610, and through the side opening 619 (which is relatively large at the scooped portion 614), as shown in FIG. 17, with the scooped portion 614 just entering the proximal end of the ureter.

Figure 18:
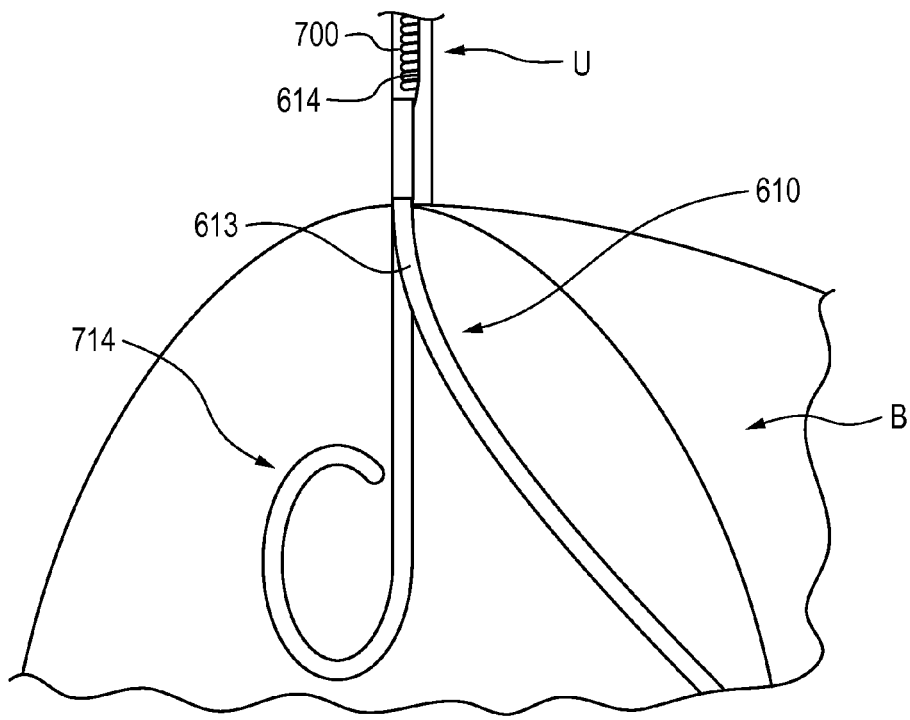
FIG. 18 is the system of FIG. 16 with the first sheath threaded over the indwelling stent partially through the ureter.

As the first sheath 610 is additionally threaded along the stent 700 (and into the ureter U, the stent 700 is urged into the cavity 618, and specifically portions of the cavity 618 defined along the central portion 613 of the first sheath 610, as best shown in FIGS. 17 and 18. As can be appreciated with reference to FIGS. 17 and 18, the formation of the first sheath 610 with the side opening 619 allows the first sheath 610 to be extended over the stent 700 with a point of initial contact just proximate to the ureter U, and without requiring the straightening of an arcuate portion or pigtail portion 714 of the stent 700 within the bladder B, which minimizes the chance of moving the stent 700 proximally and out of the kidney K until the first sheath 610 is fully threaded over the stent 700 and also extends into the kidney K, as shown in FIG. 19.

Figure 19:
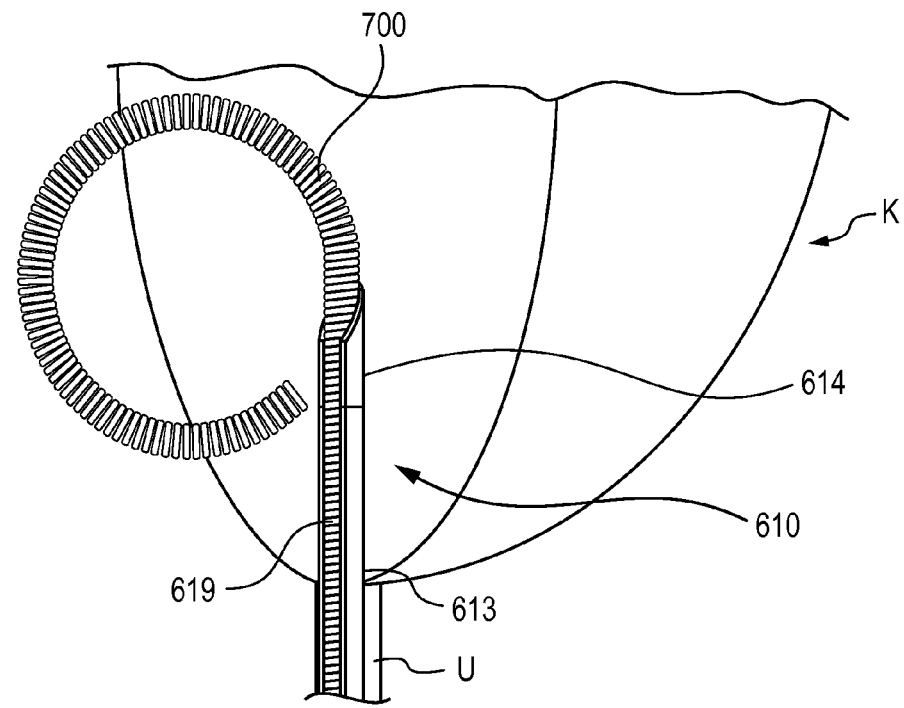
FIG. 19 is the system of FIG. 16 with the first sheath threaded over the indwelling stent into the kidney.

As shown in FIG. 19, the first sheath 610 may be threaded along the stent 700 (through the ureter U) with the stent 700 maintained in a stationary orientation until the first sheath 610 extends into the kidney K. Once the first sheath 610 enters the kidney K, the stent 700 may be withdrawn proximally (with the first sheath 610 maintained stationary) to remove the stent 700 from the kidney, ureter, and ultimately the patient.

Figure 20:
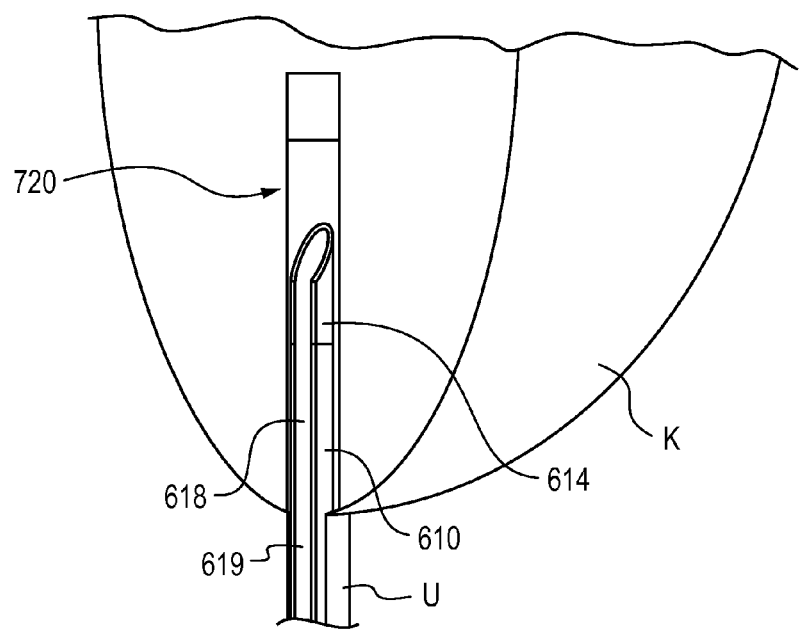
FIG. 20 is the system of FIG. 16 with the indwelling stent removed from the first sheath and a second sheath threaded over the first sheath and into the kidney.
Figure 21:
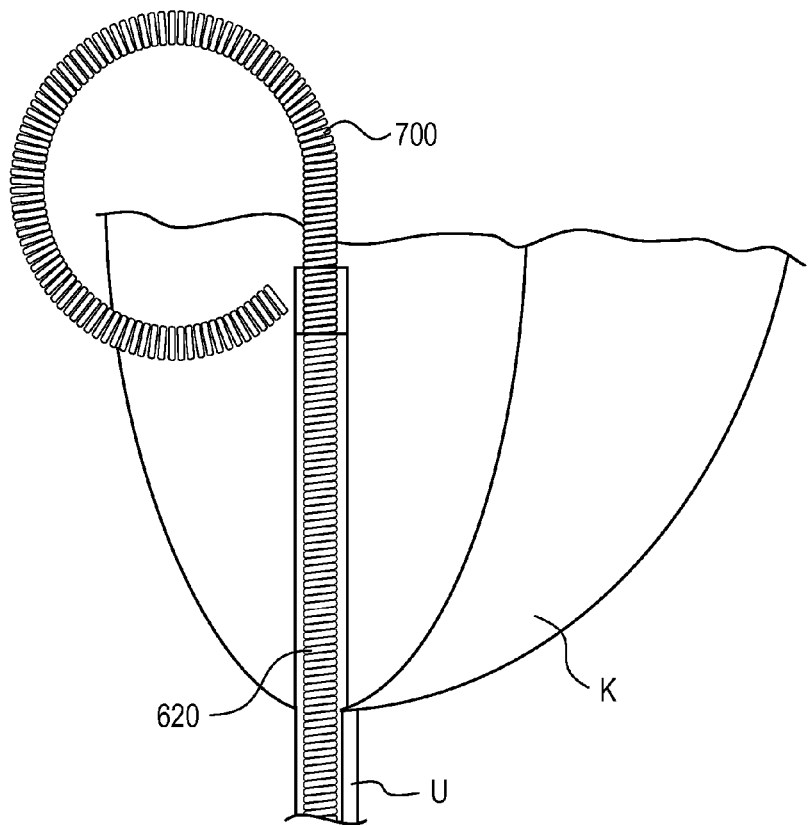
FIG. 21 is the system of FIG. 16 with a new stent threaded through the second sheath and positioned within the kidney and ureter.

In some embodiments and as shown in FIG. 20, the second sheath 620, may be pushed into the bladder B and threaded over the first sheath 610, which may be aided by a scooped portion formed at the proximal end portion of the first sheath 610 (similar to scooped portion 614 upon the distal end portion depicted and described herein). The second sheath 620 may be threaded over the first sheath 610 until the second sheath 620 enters the kidney K. Once the second sheath 620 reaches the kidney, the first sheath 610 is pulled proximally as, may be observed through a scope threaded through the second sheath 620 and removed from the kidney K, ureter U, bladder B and ultimately from the patient. Once the first sheath 610 is withdrawn from the second sheath 620, a new stent 700 (which may be like the stent 700 removed during the procedure, or may be another type of stent configured for indwelling within the ureter U (or other desired clinical location within the patient) may be threaded through the lumen of the second sheath 620, potentially with a pusher (not shown) that engages the proximal tip of the new stent 700) and into position within the ureter U, and extending into the kidney K and bladder B as desired, as shown in FIG. 21. Once the new stent 700 is properly positioned, the second stent 620 may be withdrawn.

In embodiments where only a first sheath 610 is provided in the kit, the new stent 700 may be threaded directly through the cavity 618 of the first sheath 610, which may enter the cavity 618 (of the portion of the first sheath 610 that extends into the bladder B) through a scooped portion on the proximal end portion (like scooped portion 614), when provided and/or may enter the cavity through the side opening 619, by locally stretching the side opening 619. The stent 700 may then be threaded into position through the ureter U and into the kidney K, as urged by a pusher (not shown) that also extends enters the cavity proximally of the stent 700 (either through the scooped portion or the side opening 619 of the first sheath 610). After the stent 700 is properly positioned, the first sheath 610 is pulled proximally (with the stent 700 maintained in position) and the first sheath is removed from the patient.

While the preferred embodiments of the disclosure have been described, it should be understood that the disclosure is not so limited and modifications may be made without departing from the disclosure. The scope of the invention is defined by the appended claims, and all devices that come within the meaning of the claims, either literally or by equivalence, are intended to be embraced therein.

The invention claimed is:

1. A stent comprising:
   an elongate body comprising a tightly coiled wire disposed therealong, the coiled wire spanning between a first end portion and a second end portion, and defining a lumen therethrough;
   a safety wire disposed through the lumen and fixed with respect to each of the first and second end portions of the coiled wire;
   a proximal end cap distinct from and fixed to a proximal end of the safety wire and a distal end cap distinct from and fixed to a distal end of the safety wire, each of the proximal and distal end caps are fixed with respect to the respective first and second end portions of the coiled wire;
   wherein at least one of the proximal and distal end caps comprises a first window in communication with the lumen of the coiled wire and a second window configured to receive the safety wire therethrough, and configured to allow access to the safety wire to join the safety wire and the respective end cap.

2. The stent of claim 1, wherein the proximal and distal end caps are welded to the respective first and second end portions of the coiled wire.

3. The stent of claim 1, wherein the second window extends along a portion of the length of at least one of the proximal and distal end caps.

4. The stent of claim 3, wherein the second window comprises a ledge disposed at an end portion of the second window.

5. The stent of claim 1, further comprising a cuff that is next to at least one of the proximal and distal end caps and receives the end tip of the coiled wire.

6. The stent of claim 1, wherein the proximal end cap and the distal end cap comprise a tapered profile.

7. The stent of claim 6, wherein the proximal end cap and the distal end cap each comprise a chamfered edge at a tip of the respective end cap.

8. A stent, comprising:
   an elongate central portion comprising a coiled wire disposed to define a plurality of coils disposed proximate to each other along a length of a stent between proximal and distal end portions with a lumen disposed therethrough, the plurality of coils each coiled to form a first outer diameter;

further comprising a safety wire disposed through the lumen of the stent and fixed to one or both of the proximal and distal end portions;

wherein the proximal end portion of the coiled wire comprises an outer diameter, the outer diameter being tapered at the proximal end portion of the coiled wire toward a proximal end tip upon the proximal end portion of the coiled wire;

further comprising a weld bead disposed upon the proximal end tip of the coiled wire, wherein an outer diameter of the weld bead is less than the first outer diameter but greater than the outer diameter of the proximal end tip of the coiled wire;

further comprising a grasper comprising two or more arms that extend from a control portion, wherein each of the arms are configured to extend over the proximal end tip;

wherein a maximum outer diameter of the two or more arms is equal to or smaller than the first outer diameter.

9. The stent of claim 8, wherein each of the two or more arms include a tooth that is configured to engage the proximal end tip, or the weld bead disposed upon the proximal end tip when the grasper is urged toward the proximal end portion of the coiled wire.

10. A stent comprising:
an elongate body comprising a tightly coiled wire disposed therealong, the coiled wire spanning between a first end portion and a second end portion, and defining a lumen therethrough;

a safety wire disposed through the lumen and fixed with respect to each of the first and second end portions of the coiled wire;

a proximal conical end cap fixed to a proximal end of the safety wire and a conical distal end cap fixed to a distal end of the safety wire, each of the proximal and distal end caps are fixed with respect to the respective first and second end portions of the coiled wire;

wherein at least one of the proximal and distal end caps comprises a first window in communication with the lumen of the coiled wire and a second window configured to receive the safety wire therethrough, and configured to allow access to the safety wire to join the safety wire and the respective end cap.

11. The stent of claim 10, wherein the proximal end cap is distinct from the proximal end of the safety wire and the distal end cap is distinct from the distal end of the safety wire.

12. The stent of claim 10, wherein the proximal and distal end caps are welded to the respective first and second end portions of the coiled wire.

13. The stent of claim 10, wherein the second window extends along a portion of the length of at least one of the proximal and distal end caps.

14. The stent of claim 13, wherein the second window comprises a ledge disposed at an end portion of the second window.

15. The stent of claim 10, further comprising a cuff that is next to at least one of the proximal and distal end caps and receives the end tip of the coiled wire.

16. The stent of claim 10, wherein the proximal end cap and the distal end cap each comprise a chamfered edge at a tip of the respective end cap.

* * * * *